(12) United States Patent
Stolnik-Trenkic et al.

(10) Patent No.: US 11,583,587 B2
(45) Date of Patent: Feb. 21, 2023

(54) POLYMER

(71) Applicant: VECTURA LIMITED, Chippenham (GB)

(72) Inventors: Snjezana Stolnik-Trenkic, Chippenham (GB); Giuseppe Mantovani, Chippenham (GB); Alejandro Nieto Orellana, Chippenham (GB)

(73) Assignee: Vectura Limited

( * ) Notice: Subject to any disclaimer, the term of this patent is extended or adjusted under 35 U.S.C. 154(b) by 1060 days.

(21) Appl. No.: 16/321,615

(22) PCT Filed: Jul. 28, 2017

(86) PCT No.: PCT/EP2017/069236
§ 371 (c)(1),
(2) Date: Jan. 29, 2019

(87) PCT Pub. No.: WO2018/020034
PCT Pub. Date: Feb. 1, 2018

(65) Prior Publication Data
US 2021/0138074 A1 May 13, 2021

(30) Foreign Application Priority Data
Jul. 29, 2016 (GB) .................................... 1613166

(51) Int. Cl.
*A61K 47/60* (2017.01)
*A61K 9/00* (2006.01)
*A61K 39/395* (2006.01)
*C08G 69/42* (2006.01)

(52) U.S. Cl.
CPC ............ *A61K 47/60* (2017.08); *A61K 9/0075* (2013.01); *A61K 39/395* (2013.01); *C08G 69/42* (2013.01)

(58) Field of Classification Search
CPC ....... A61K 47/60; A61K 9/0075; C08G 69/42
See application file for complete search history.

(56) References Cited

U.S. PATENT DOCUMENTS

2010/0104512 A1\* 4/2010 Felder-Flesch ......... A61P 25/00
424/9.1

FOREIGN PATENT DOCUMENTS

| JP | 2005232061 A | 9/2005 |
| WO | 2004101600 A2 | 11/2004 |
| WO | 2015160770 A1 | 10/2015 |

OTHER PUBLICATIONS

USPTO structure search, Jun. 2022.\*
International Search Report and Written Opinion for PCT/EP2017/069236 dated Sep. 29, 2017.

\* cited by examiner

*Primary Examiner* — Gregory Listvoyb
(74) *Attorney, Agent, or Firm* — Barnes & Thornburg LLP; Ryan P. Cox (57) ABSTRACT

A PEGylated polymer is disclosed according to Formula 1 wherein n is any integer from 4 to 200 monomers, and R is a polymer chain comprising a 4 to 200-monomer moiety.

11 Claims, 7 Drawing Sheets

POLYMER

CROSS-REFERENCE TO RELATED APPLICATIONS

This application is a United States national stage of International Application No. PCT/EP2017/069236, filed Jul. 28, 2017, which was published as International Publication No. WO 2018/020034, and which claims benefit of Great Britain Application No. 1613166.6, filed Jul. 29, 2016, the entire contents of which are hereby expressly incorporated herein by reference.

INTRODUCTION

This application relates to a polymer for use in dry powder formulations and methods for the preparation of said polymer. In particular, this application relates to a polymer for use in protein-based dry powder formulations.

BACKGROUND

Pulmonary administered therapeutic proteins have considerable clinical potential for treating local and systemic diseases.

These potential benefits can be limited by poor protein conformational stability, potential immunogenicity, and high degrees of protein degradation by proteolytic enzymes. These factors remain significant challenges to the successful pulmonary delivery of protein therapeutics.

Furthermore, most of the inhalation products currently available on the market use lactose as a carrier material. Potential side-reactions occurring at the sugar reducing end of lactose, e.g. Maillard reaction, renders this traditional carrier as unsuitable for formulations that contain primary amino groups, such as peptides and proteins. In an attempt to circumvent these side-reaction problems, non-reducing sugars such as trehalose have been extensively investigated as potential alternatives in inhalable dry powders. Due to the highly hygroscopic and aggregative nature of the amorphous form of trehalose, high concentrations of this sugar typically result in poor aerosolisation properties.

The design of polymer-protein nanosystems represent a potentially effective strategy to overcome barriers associated with the pulmonary delivery of proteins such as protein stability and clearance by proteolytic enzymes in the lungs or immunogenicity. Typically, polymers are covalently conjugated to proteins—e.g. in PEGylated protein therapeutics. However, as each therapeutic protein possesses unique chemistries and reactivity, this approach requires synthetic protocols that need to be developed on a case-by-case basis and often result in loss of the protein intended bioactivity. Within this context, nanocomplexes where synthetic polymers bind to proteins by non-covalent interactions are emerging as very valuable alternatives. However, the size of these polymer-protein nanocomplexes has, until now, precluded their efficient use in the lungs.

Consequently, there remains a need for a clinically accepted polymer that will ensure improved protein-stability, low immunogenicity and/or negligible protein degradation whilst remaining suitable for administration to the lung.

SUMMARY OF THE INVENTION

We disclose an improved copolymer with linear or miktoarm macromolecular architectures according to the structure immediately below (formula 1):

1 wherein n is any integer from 4 to 200 monomers, and R comprises a 4 to 200-monomer moiety selected from the group consisting of alanine, 3-alanine, arginine, asparagine, aspartic acid, citrulline, cystine, cysteine, cystathionine, glutamic acid, glutamine, glycine, histidine, homocysteine, hydroxyproline, hydroxylysine, isoleucine, leucine, lysine, methionine, ornithine, phenylalanine, phosphoserine, proline, pyrrolysine, serine, selenocysteine, threonine, tryptophan, tyrosine, valine, 4-aminobutyric acid or combinations thereof.

Unlike the prior art which uses either ester bonding, aspartic acid-phenylalanine or leucine monomers for use with a small molecule, the polymer according to the invention can be non-covalently complexed with a physiologically active substance such as proteins (or peptides) to generate well-defined nano-sized assemblies suitable for formulation as a dry powder. In particular, the improved copolymer removes the need to form ester bond(s) or conjugation with a physiologically active substance and instead relies upon non-covalent interaction whilst achieving improved protein-stability (as compared to the equivalent protein absent the protecting polymer according to the invention), reduced immunogenicity (as compared to the equivalent protein absent the protecting polymer according to the invention) and reduced or negligible protein degradation whilst remaining suitable for administration to the lung (as compared to the equivalent protein absent the protecting polymer according to the invention).

DETAILED DESCRIPTION OF INVENTION

When used herein, the word substantially means at least a third of the monomers by number. When used herein, the word predominantly means at least half the monomers by number. When used herein, the word essentially means at least two-thirds of the monomers by number.

In one embodiment a compound according to formula 1 is disclosed wherein n is any integer from 4 to 200 monomers, and R comprises a 4 to 200-monomer moiety selected from the group consisting of alanine, 3-alanine, arginine, asparagine, aspartic acid, citrulline, cystine, cysteine, cystathionine, glutamic acid, glutamine, glycine, histidine, homocysteine, hydroxyproline, hydroxylysine, isoleucine, leucine, lysine, methionine, ornithine, phenylalanine, phosphoserine, proline, pyrrolysine, serine, selenocysteine, threonine, tryptophan, tyrosine, valine, 4-aminobutyric acid or combinations thereof.

When used herein, the term physiologically active substance means any active ingredient or active substance, in particular, a substance which produces a physiological response when it binds to a cellular receptor or modifies a physiological process.

In one embodiment a compound according to formula 1 is disclosed wherein R comprises a 4 to 200-monomer moiety, preferably wherein the last four terminal monomers are the same amino acid.

In one embodiment a compound according to formula 1 is disclosed wherein R comprises a 5 to 175-monomer moiety, preferably wherein the last four terminal monomers are the same amino acid.

In one embodiment a compound according to formula 1 is disclosed wherein R comprises a 6 to 150-monomer moiety, preferably wherein the last four terminal monomers are the same amino acid.

In one embodiment a compound according to formula 1 is disclosed wherein R comprises a 7 to 125-monomer moiety, preferably wherein the last four terminal monomers are the same amino acid.

In one embodiment a compound according to formula 1 is disclosed wherein R comprises an 8 to 100-monomer moiety, preferably wherein the last four terminal monomers are the same amino acid.

In one embodiment a compound according to formula 1 is disclosed wherein R comprises a 9 to 75-monomer moiety, preferably wherein the last four terminal monomers are the same amino acid.

In one embodiment a compound according to formula 1 is disclosed wherein R comprises a 9 to 50-monomer moiety, preferably wherein the last four terminal monomers are the same amino acid.

In one embodiment a compound according to formula 1 is disclosed wherein R comprises a 10 to 40-monomer moiety, preferably wherein the last four terminal monomers are the same amino acid.

In one embodiment a compound according to formula 1 is disclosed wherein R comprises a 10 to 30-monomer moiety, preferably wherein the last four terminal monomers are the same amino acid.

In one embodiment, a compound according to formula 1 is disclosed wherein R comprises substantially alanine monomers, alternatively wherein R comprises predominantly alanine monomers, alternatively wherein R comprises essentially alanine monomers.

In one embodiment, a compound according to formula 1 is disclosed wherein R comprises substantially β-alanine monomers, alternatively wherein R comprises predominantly β-alanine monomers, alternatively wherein R comprises essentially β-alanine monomers.

In one embodiment, a compound according to formula 1 is disclosed wherein R comprises substantially arginine monomers, alternatively wherein R comprises predominantly arginine monomers, alternatively wherein R comprises essentially arginine monomers.

In one embodiment, a compound according to formula 1 is disclosed wherein R comprises substantially asparagine monomers, alternatively wherein R comprises predominantly asparagine monomers, alternatively wherein R comprises essentially asparagine monomers.

In one embodiment, a compound according to formula 1 is disclosed wherein R comprises substantially aspartic acid monomers, alternatively wherein R comprises predominantly aspartic acid monomers, alternatively wherein R comprises essentially aspartic acid monomers.

In one embodiment, a compound according to formula 1 is disclosed wherein R comprises substantially citrulline monomers, alternatively wherein R comprises predominantly citrulline monomers, alternatively wherein R comprises essentially citrulline monomers.

In one embodiment, a compound according to formula 1 is disclosed wherein R comprises substantially cystine monomers, alternatively wherein R comprises predominantly cystine monomers, alternatively wherein R comprises essentially cystine monomers.

In one embodiment, a compound according to formula 1 is disclosed wherein R comprises substantially cysteine monomers, alternatively wherein R comprises predominantly cysteine monomers, alternatively wherein R comprises essentially cysteine monomers.

In one embodiment, a compound according to formula 1 is disclosed wherein R comprises substantially cystathionine monomers, alternatively wherein R comprises predominantly cystathionine monomers, alternatively wherein R comprises essentially alanine monomers.

In one embodiment, a compound according to formula 1 is disclosed wherein R comprises substantially glutamic acid monomers, alternatively wherein R comprises predominantly glutamic acid monomers, alternatively wherein R comprises essentially glutamic acid monomers.

In one embodiment, a compound according to formula 1 is disclosed wherein R comprises substantially glutamine monomers, alternatively wherein R comprises predominantly glutamine monomers, alternatively wherein R comprises essentially glutamine monomers.

In one embodiment, a compound according to formula 1 is disclosed wherein R comprises substantially glycine monomers, alternatively wherein R comprises predominantly glycine monomers, alternatively wherein R comprises essentially glycine monomers.

In one embodiment, a compound according to formula 1 is disclosed wherein R comprises substantially histidine monomers, alternatively wherein R comprises predominantly histidine monomers, alternatively wherein R comprises essentially histidine monomers.

In one embodiment, a compound according to formula 1 is disclosed wherein R comprises substantially homocysteine monomers, alternatively wherein R comprises predominantly homocysteine monomers, alternatively wherein R comprises essentially homocysteine monomers.

In one embodiment, a compound according to formula 1 is disclosed wherein R comprises substantially hydroxyproline monomers, alternatively wherein R comprises predominantly hydroxyproline monomers, alternatively wherein R comprises essentially hydroxyproline monomers.

In one embodiment, a compound according to formula 1 is disclosed wherein R comprises substantially hydroxylysine monomers, alternatively wherein R comprises predominantly hydroxylysine monomers, alternatively wherein R comprises essentially hydroxylysine monomers.

In one embodiment, a compound according to formula 1 is disclosed wherein R comprises substantially isoleucine monomers, alternatively wherein R comprises predominantly isoleucine monomers, alternatively wherein R comprises essentially isoleucine monomers.

In one embodiment, a compound according to formula 1 is disclosed wherein R comprises substantially leucine monomers, alternatively wherein R comprises predominantly leucine monomers, alternatively wherein R comprises essentially leucine monomers.

In one embodiment, a compound according to formula 1 is disclosed wherein R comprises substantially lysine monomers, alternatively wherein R comprises predominantly lysine monomers, alternatively wherein R comprises essentially lysine monomers.

In one embodiment, a compound according to formula 1 is disclosed wherein R comprises substantially methionine monomers, alternatively wherein R comprises predominantly methionine monomers, alternatively wherein R comprises essentially methionine monomers.

In one embodiment, a compound according to formula 1 is disclosed wherein R comprises substantially ornithine monomers, alternatively wherein R comprises predominantly ornithine monomers, alternatively wherein R comprises essentially ornithine monomers.

In one embodiment, a compound according to formula 1 is disclosed wherein R comprises substantially phenylalanine monomers, alternatively wherein R comprises predominantly phenylalanine monomers, alternatively wherein R comprises essentially phenylalanine monomers.

In one embodiment, a compound according to formula 1 is disclosed wherein R comprises substantially phosphoserine monomers, alternatively wherein R comprises predominantly phosphoserine monomers, alternatively wherein R comprises essentially phosphoserine monomers.

In one embodiment, a compound according to formula 1 is disclosed wherein R comprises substantially proline monomers, alternatively wherein R comprises predominantly proline monomers, alternatively wherein R comprises essentially proline monomers.

In one embodiment, a compound according to formula 1 is disclosed wherein R comprises substantially pyrrolysine monomers, alternatively wherein R comprises predominantly pyrrolysine monomers, alternatively wherein R comprises essentially pyrrolysine monomers.

In one embodiment, a compound according to formula 1 is disclosed wherein R comprises substantially serine monomers, alternatively wherein R comprises predominantly serine monomers, alternatively wherein R comprises essentially serine monomers.

In one embodiment, a compound according to formula 1 is disclosed wherein R comprises substantially selenocysteine monomers, alternatively wherein R comprises predominantly selenocysteine monomers, alternatively wherein R comprises essentially selenocysteine monomers.

In one embodiment, a compound according to formula 1 is disclosed wherein R comprises substantially threonine monomers, alternatively wherein R comprises predominantly threonine monomers, alternatively wherein R comprises essentially threonine monomers.

In one embodiment, a compound according to formula 1 is disclosed wherein R comprises substantially tryptophan monomers, alternatively wherein R comprises predominantly tryptophan monomers, alternatively wherein R comprises essentially tryptophan monomers.

In one embodiment, a compound according to formula 1 is disclosed wherein R comprises substantially tyrosine monomers, alternatively wherein R comprises predominantly tyrosine monomers, alternatively wherein R comprises essentially tyrosine monomers.

In one embodiment, a compound according to formula 1 is disclosed wherein R comprises substantially valine monomers, alternatively wherein R comprises predominantly valine monomers, alternatively wherein R comprises predominantly valine monomers.

In one embodiment, a compound according to formula 1 is disclosed wherein R comprises substantially 4-aminobutyric acid monomers, alternatively wherein R comprises predominantly 4-aminobutyric acid monomers, alternatively wherein R comprises predominantly 4-aminobutyric acid monomers.

In one embodiment a compound according to formula 1 is disclosed wherein R is a linear polymer.

In one preferred embodiment a compound according to formula 1 is disclosed wherein R is a linear polymer and wherein R is not initiated by an aromatic hydrocarbon group or an aromatic heterocyclic group.

In one preferred embodiment a compound according to formula 1 is disclosed wherein R is a linear polymer and wherein R does not contain an aromatic hydrocarbon group or an aromatic heterocyclic group.

In one embodiment a compound according to formula 1 is disclosed wherein R comprises a branching molecule.

In one embodiment a compound according to formula 1 is disclosed wherein the branching molecule comprises gallic acid, preferably wherein the branching molecule is gallic acid.

In one embodiment a compound according to formula 1 is disclosed wherein R is initiated by gallic acid.

In one embodiment a compound according to formula 1 is disclosed wherein R is a branched polymer.

In one embodiment a compound according to formula 1 is disclosed further comprising a protein held by non-covalent interaction with the compound according to formula 1.

In one embodiment a pharmaceutical composition comprising a compound according to formula 1 is disclosed further comprising a protein held by non-covalent interaction with the compound according to formula 1.

In one embodiment a pharmaceutical composition comprising a compound according to formula 1 is disclosed further comprising a protein held by non-covalent interaction with the compound according to formula 1 wherein the protein is an antibody.

In one embodiment a pharmaceutical composition comprising a compound according to formula 1 is disclosed further comprising a protein held by non-covalent interaction with the compound according to formula 1 wherein the protein is a chimeric antibody or a humanised antibody or a human antibody.

In one embodiment a pharmaceutical composition comprising a compound according to formula 1 is disclosed further comprising an antibody held by non-covalent interaction with the compound according to formula 1 wherein the antibody is selected from either Omalizumab, ALX-0171, Reslizumab, Mepolizumab, Benralizumab, Brodalumab, Secukinumb, Lebrikizumab, Tralokinumab, Dupilumab, FG3019, STX-100, SAR156597, Canakinumab, MEDI-557, Freolimumab, Cetuximab, Bevacizumab, ESBA105 or Flebogamma.

In one embodiment a pharmaceutical composition comprising a compound according to formula 1 is disclosed further comprising a peptide held by non-covalent interaction with the compound according to formula 1.

In one embodiment the use of the compound according to formula 1 is disclosed for reducing the immunogenicity of a protein or peptide held by non-covalent interaction with the compound according to formula 1.

In one embodiment the use of the compound according to formula 1 is disclosed for improved stability of a protein or peptide held by non-covalent interaction with the compound according to formula 1.

In one embodiment the use of the compound according to formula 1 is disclosed which does form an ester bond with a physiologically active substance.

In one embodiment the use of the compound according to formula 1 is disclosed which does form a conjugate of physiologically active substance.

In one embodiment the use of the compound according to formula 1 in the manufacture of a medicament for the treatment of a respiratory disease is disclosed, preferably wherein the respiratory disease is chronic obstructive pulmonary disease (COPD), asthma, cystic fibrosis (CF) or related airway diseases.

In one preferred embodiment a method of treating a respiratory disease, comprising administering a pharmaceutical composition comprising the compound according to according to formula 1 and a physiologically active substance is disclosed, wherein the physiologically active substance is held by the compound according to formula 1 with non-covalent interaction.

In one preferred embodiment a pharmaceutical kit comprising the compound according to formula 1 and a physiologically active substance is disclosed, wherein the physiologically active substance is held by the compound according to according to formula 1 with non-covalent interaction.

The copolymers disclosed possess linear n-R or miktoarm n-R structures where the length of the hydrophilic n block (mPEG) is kept constant and that of protein-binding $R_1$, $R^2$ and $R^3$ arms was systemically varied. The number of repeating units in $R^1$, $R^2$ and $R^3$ block arms varied from 10 to 30 units, to give a library of Linear n-R with 10 units (referred to as L10) and n-R with 30 units (L30); and Miktoarm n-$(R10)_3$ (referred to as M30) and n-$(R30)_3$ (M90) copolymers. In one preferred embodiment a compound according to formula 1 is disclosed, wherein n is any integer from 4 to 200 monomers, and R is a polymer chain comprising a 10 to 30-monomer moiety selected from the group consisting of alanine, 3-alanine, arginine, asparagine, aspartic acid, citrulline, cystine, cysteine, cystathionine, glutamic acid, glutamine, glycine, histidine, homocysteine, hydroxyproline, hydroxylysine, isoleucine, leucine, lysine, methionine, ornithine, phenylalanine, phosphoserine, proline, pyrrolysine, serine, selenocysteine, threonine, tryptophan, tyrosine, valine, 4-aminobutyric acid or combinations thereof. Preferably wherein the 10 to 30-monomer moiety is present as from L10 to L30, preferably M30 or preferably a M90 configuration. Preferably wherein the polymer chain comprises glutamic acid.

In one preferred embodiment the use of the compound of formula 1 for reducing the immunogenicity of a physiologically active substance, for example a protein or peptide, held by the compound with non-covalent interaction is disclosed, wherein n is any integer from 4 to 200 monomers, and R is a polymer chain comprising a 4 to 200-monomer moiety selected from the group consisting of alanine, β-alanine, arginine, asparagine, aspartic acid, citrulline, cystine, cysteine, cystathionine, glutamic acid, glutamine, glycine, histidine, homocysteine, hydroxyproline, hydroxylysine, isoleucine, leucine, lysine, methionine, ornithine, phenylalanine, phosphoserine, proline, pyrrolysine, serine, selenocysteine, threonine, tryptophan, tyrosine, valine, 4-aminobutyric acid or combinations thereof. Preferably wherein the polymer chain R comprises a L10 to L30-monomer moiety, preferably R comprises a M30 or preferably a M90 configuration. Preferably wherein the polymer chain comprises glutamic acid.

In one preferred embodiment the use of the compound of formula 1 for improved stability of a physiologically active substance, for example a protein or peptide, held by the compound with non-covalent interaction is disclosed, wherein n is any integer from 4 to 200 monomers, and R is a polymer chain comprising a 4 to 200-monomer moiety selected from the group consisting of alanine, β-alanine, arginine, asparagine, aspartic acid, citrulline, cystine, cysteine, cystathionine, glutamic acid, glutamine, glycine, histidine, homocysteine, hydroxyproline, hydroxylysine, isoleucine, leucine, lysine, methionine, ornithine, phenylalanine, phosphoserine, proline, pyrrolysine, serine, selenocysteine, threonine, tryptophan, tyrosine, valine, 4-aminobutyric acid or combinations thereof. Preferably wherein the polymer chain R comprises a L10 to L30-monomer moiety, preferably R comprises a M30 or preferably a M90 configuration. Preferably wherein the polymer chain comprises glutamic acid.

In one preferred embodiment a compound according to formula 2 below is disclosed with protein-binding arms $R^1$, $R^2$ and $R^3$, each protein-binding arm assuming an individualised, or shared, R embodiment as described herein.

2

In one embodiment the use of the compound according to formula 2 is disclosed for reducing the immunogenicity of a protein or peptide held by non-covalent interaction with the compound according to formula 2.

In one embodiment the use of the compound according to formula 2 is disclosed for improved stability of a protein or peptide held by non-covalent interaction with the compound according to formula 1.

FIGURES

FIG. 1 illustrates the extent of protein incorporated into the dry powders. All dry powders contain leucine (10% w/w), phosphate buffer salts (6.6% w/w) and trehalose (up to 100% w/w). L10, L30, M30 and M90 correspond to dry powders containing polymer-protein nanocomplexes (10% w/w) where the polymer is L10, L30, M30 or M90, respectively. Samples named "lysozyme" contained no polymer (lysozyme 5% w/w). These data demonstrate no discernable difference between L10 and M30 with respect to the encapsulation efficiencies. In order to make an accurate comparison it is necessary to compare polymers with the same number of amino acids; in essence, the number braches does not appear to matter; it is the length of the chain that imparts an effect. One-way ANOVA was used for statistical analysis. * $p<0.1$, * $p<0.001$, ** $p<0.0001$.

FIG. 2 illustrates the Fine Particle Fraction (solid bars) and Emitted Dose (hatched bars) for dry powder formulations. All dry powders contain leucine (10% w/w), phosphate buffer salts (6.6% w/w) and trehalose (up to 100% w/w). L10, L30, M30 and M90 correspond to dry powders containing polymer-protein nanocomplexes (10% w/w) where the polymer is L10, L30, M30 or M90, respectively. Samples named "lysozyme" contained no polymer (lysozyme 5% w/w). One-way ANOVA was used for statistical analysis. * $p<0.1$, * $p<0.001$, ** $p<0.0001$.

FIG. 3 illustrates the particle size distribution of nanocomplexes before spray-drying as measured by nanoparticle tracking analysis wherein M90 demonstrates a bimodal size distribution and unimodal in distributions for the other polymers.

Figure 3:
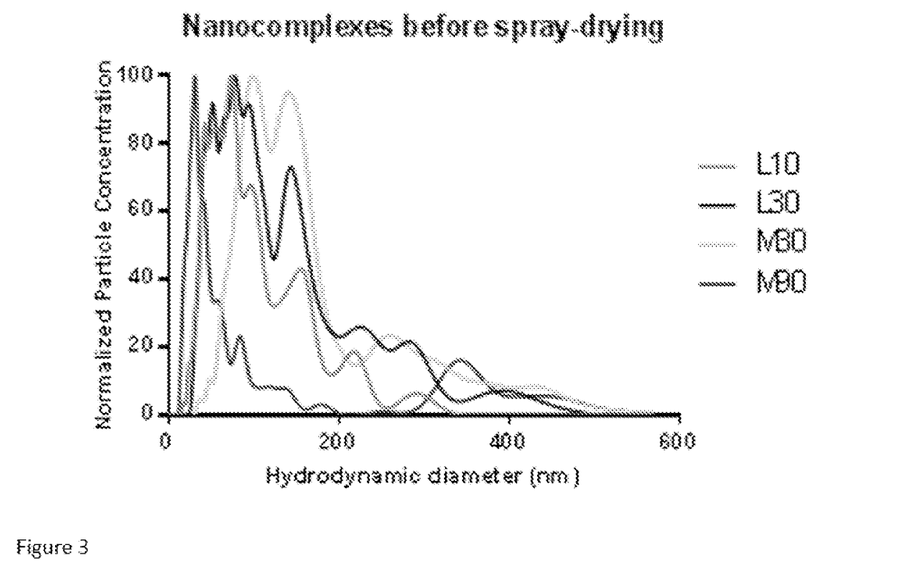
Figure 4:
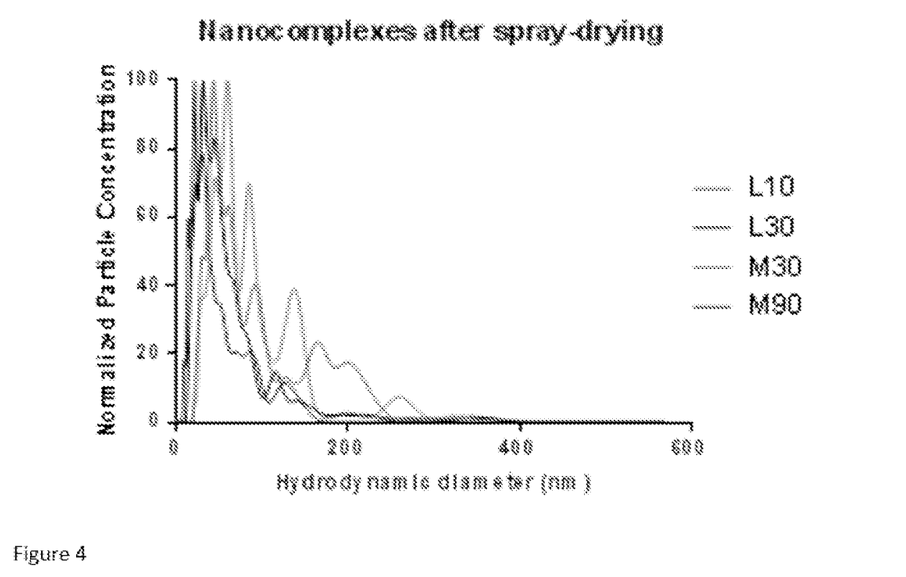

FIG. 4 illustrates the particle size distribution of nanocomplexes recovered from trehalose-leucine-based dry powders after incubation in Phosphate Buffer (PB) (10 mM, pH 7.4) for 1 h as measured by nanoparticle tracking analysis clearly demonstrating a size reduction with respect to FIG. 3.

Figure 5:
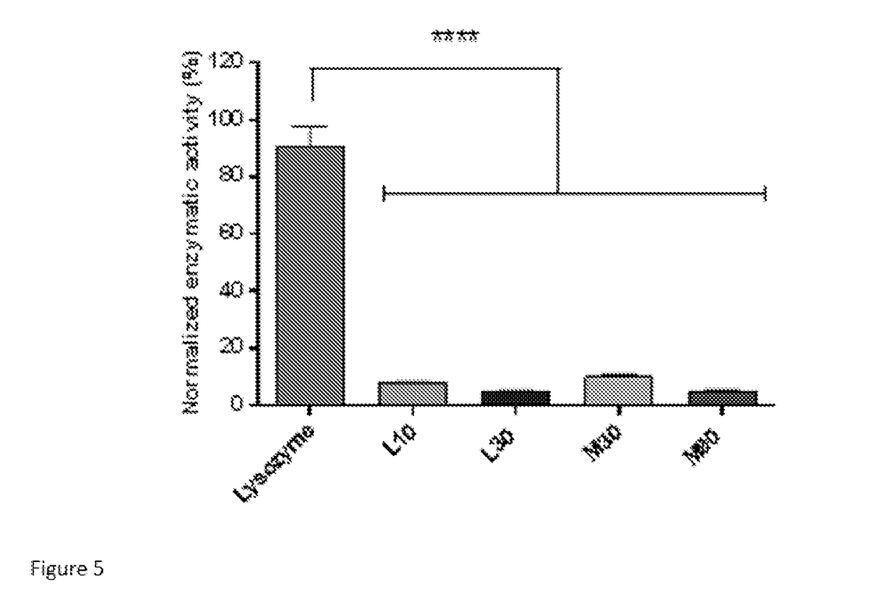

FIG. 5 demonstrates lysozyme activity after incubation of the dry powders in phosphate buffer (PB: 10 mM, pH 7.4) clearly demonstrating that these polymers are effective in masking the protein activity; demonstrating the transient nature of the masking mechanism. All formulations contained leucine (10% w/w), phosphate buffer salts (6.6% w/w) and trehalose (up to 100% w/w). All experiments were carried out in triplicate (n=3) and data are presented as mean±SD. One-way ANOVA was used for statistical analysis. **** p<0.0001.

Figure 6:
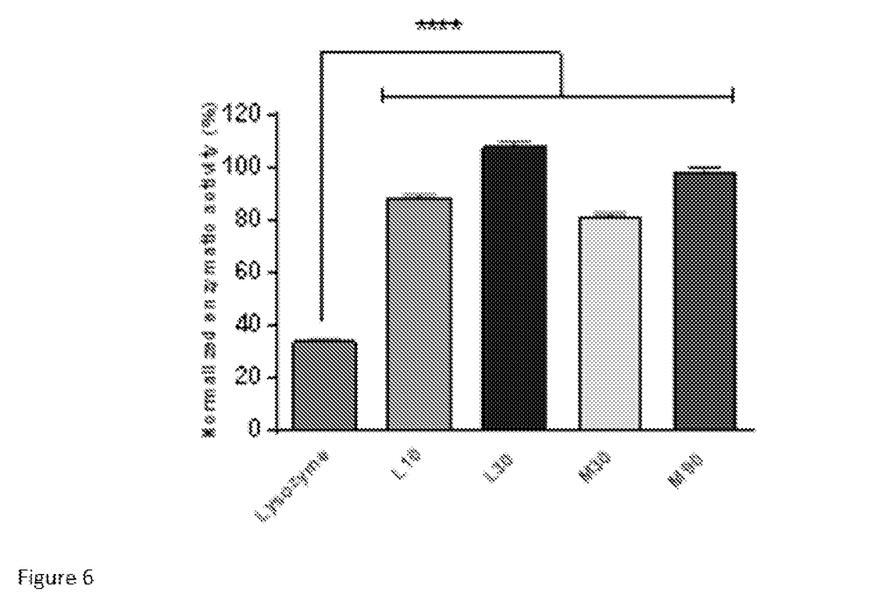

FIG. 6 demonstrates lysozyme activity after incubation of the dry powders in presence of trypsin for 3 h in PB (10 mM, pH 7.4) followed by the addition of poly(allyl amine) for 1 h to promote the disassembly of the nanocomplexes showing release the protein and demonstrate residual activity. All formulations contained leucine (10% w/w), phosphate buffer salts (6.6% w/w) and trehalose (up to 100% w/w). All experiments were carried out in triplicate and data are presented as mean±SD. One-way ANOVA was used for statistical analysis. **** p<0.0001.

Figure 7:
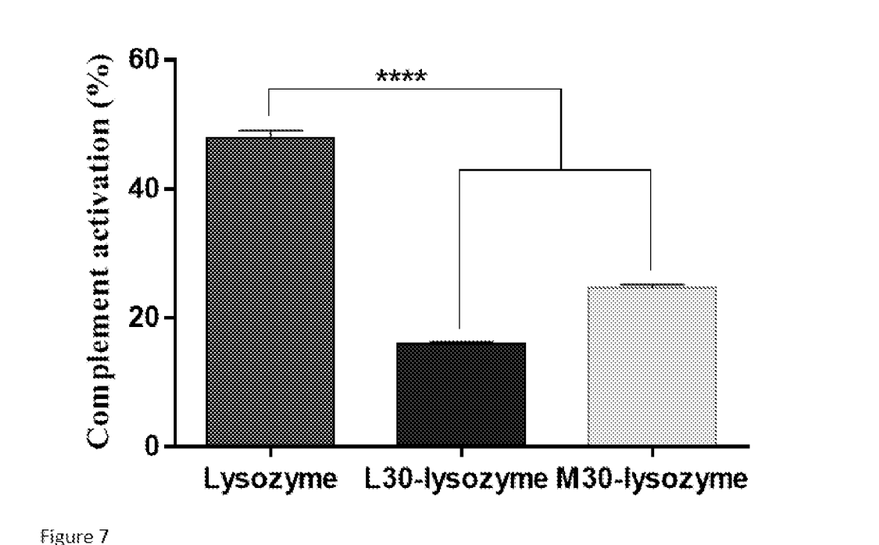

FIG. 7 demonstrates Complement activation at 37° C. by polymer (L30 or M30)-lysozyme nanocomplexes and free lysozyme. Both (L30 or M30)-lysozyme nanocomplexes demonstrate excellent reduction in complement activity. One-way ANOVA was used for statistical analysis. **** p<0.0001. Lysozyme molecule concentration was 1116 μg/mL (78 μM) and Polymer molecular concentration was 777 μg/mL (111 μM).

Figure 8:
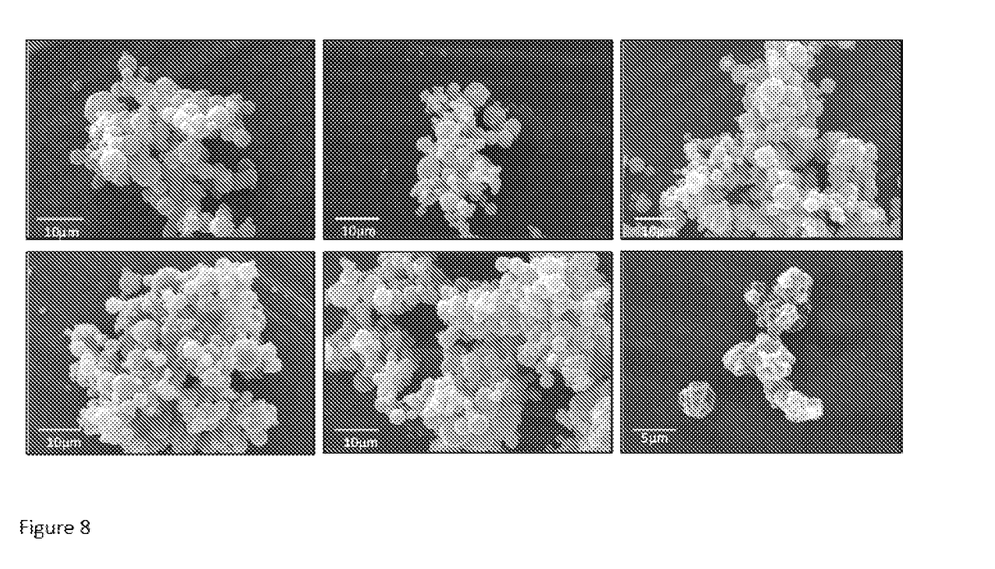

FIG. 8 demonstrates SEM images of dry powders before [Top row of photos] and after [Bottom row of photos] spraying using a PennCentury nozzle. All dry powders contain leucine (10% w/w), buffer salts (6.6% w/w) and trehalose (up to 100% w/w). Linear copolymer corresponds to dry powders containing linear mPEG$_{2k}$-/in-GA$_{30}$ (L30): lysozyme nanocomplexes (10% w/w) [First column of photos]. Miktoarm copolymer corresponds to dry powders containing miktoarm mPEG$_{2k}$-mik-(GA$_{10}$)$_{30}$ (M30):lysozyme nanocomplexes (10% w/w) [Second column of photos]. Free lysozyme corresponds to dry powders containing lysozyme (NO polymer) (5% w/w) [Third column of photos].

Figure 9:
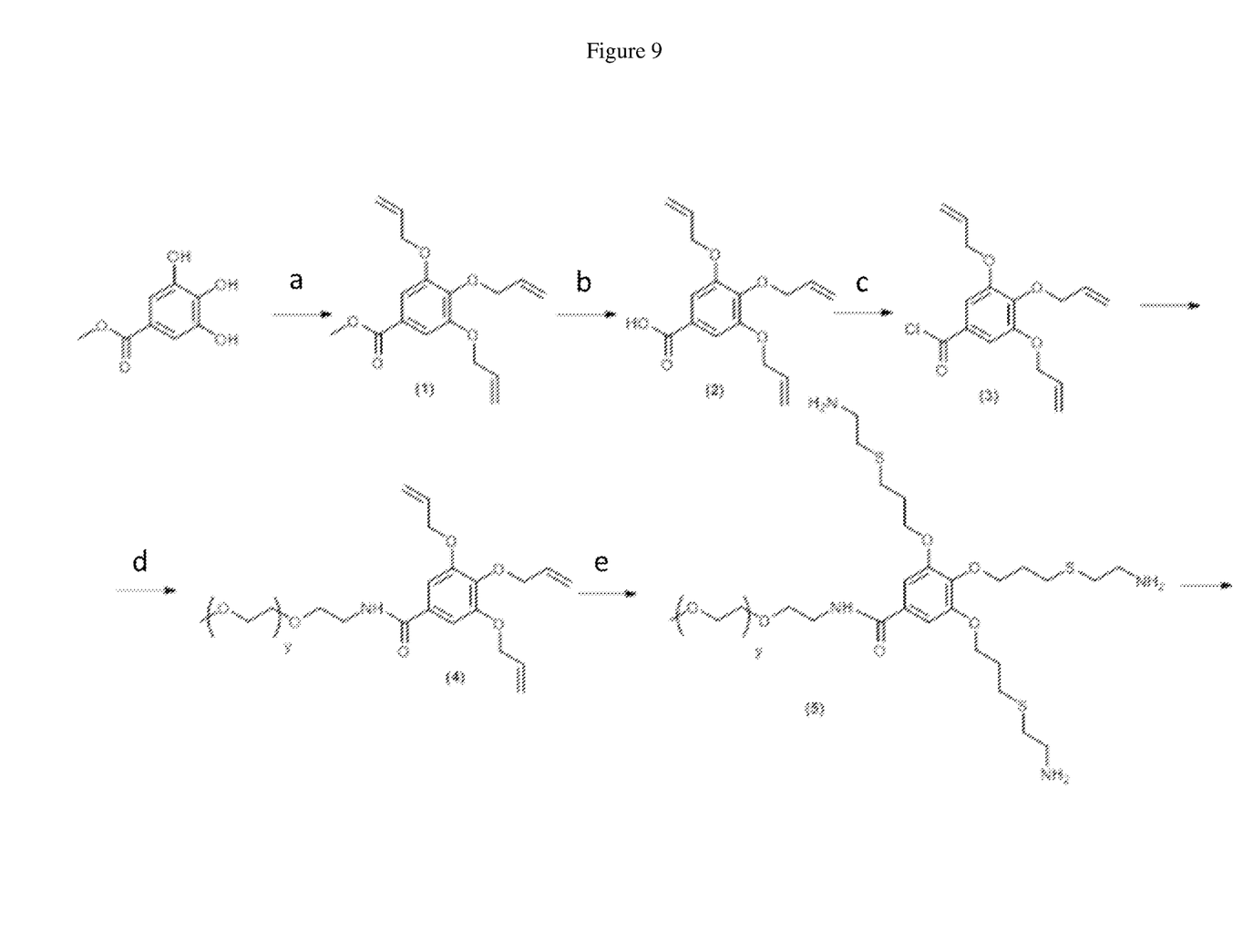

FIG. 9 demonstrates a possible synthesis route explaining the reactions and conditions: (a) allyl bromide, K2CO3, acetonitrile, heated to reflux, 3 h (b) NaOH, MeOH/CH2Cl2, 14 h (c) oxallyl chloride, DMF, CH2Cl2, 1 h (d) methoxypolyethylene glycol amine 2.0 kDa, triethylamine, CH2Cl2, overnight (e) cysteamine hydrochloride, DPAP, MeOH, UV, 3 h (f) and (g) (1) γ-benzyl-L-glutamate NCA, THF, 0° C., 5 days and (2) NaOH, H$_2$O/THF, 2 days.

DESCRIPTION OF THE POLYMER

The polymer of the invention is not limited to the illustrated embodiments.

In one embodiment, n×MW$_{(ethylene\ oxide)}$ preferably has a number average molecular weight from 250 Daltons to 100,000 Daltons, preferably n×MW$_{(ethylene\ oxide)}$ has a weight average molecular weight from 50,000 Daltons to 80,000 Daltons, or more preferably n has a weight average molecular weight from 60,000 Daltons to 75,000 Daltons. In one embodiment, n×MW$_{(ethylene\ oxide)}$ preferably has a number average molecular weight from 1000 to 5000 Daltons, more preferably 10000 to 20000 Daltons.

In one embodiment, n is any integer from 4 to 200 monomers, preferably from 10 to 175 monomers, preferably from 20 to 150 monomers, preferably from 30 to 125 monomers, preferably from 40 to 100 monomers, preferably from 50 to 75 monomers.

Pharmaceutical Additives

In one embodiment, the pharmaceutical composition comprising the compound according to formula 1 may comprise an additive material, such as a force control agent. A force control agent is an additive material which reduces the cohesion between the fine particles within the powder formulation, thereby promoting deagglomeration upon dispensing of the powder from the dry powder inhaler. Suitable force control agents are disclosed in WO 1996 023485 and they preferably consist of physiologically acceptable material, despite the fact that the material may not always reach the lung.

The force control agent may comprise or consist of one or more compounds selected from amino acids and derivatives thereof, and peptides and derivatives thereof, the peptides preferably having a molecular weight from 0.25 to 1000 KDa. Amino acids, peptides and derivatives of peptides are physiologically acceptable and give acceptable release or deagglomeration of the particles of active material on inhalation. Where the force control agent comprises an amino acid, it may be one or more of any of the following amino acids: leucine, isoleucine, lysine, valine, methionine, and phenylalanine. The force control agent may be a salt or a derivative of an amino acid, for example aspartame or acesulfame K. The D- and DL-forms of amino acids may also be used.

Force control agents which are particularly suitable for use in the present invention include, amino acids including leucine, lysine, arginine, histidine, cysteine and their derivatives, lecithin and phospholipids. The inclusion of these force control agents may improve the efficacy of the pharmaceutically active material for treating respiratory disorders such as COPD, asthma or CF.

Force control agents may include one or more water soluble substances. This helps absorption of the force control agent by the body if it reaches the lower lung. The force control agent may include dipolar ions, which may be zwitterions. It is also advantageous to include a spreading agent as a force control agent, to assist with the dispersal of the composition in the lungs.

Suitable spreading agents include surfactants such as known lung surfactants (e.g. ALEC, Registered Trade Mark) which comprise phospholipids, for example, mixtures of DPPC (dipalmitoyl phosphatidylcholine) and PG (phosphatidylglycerol). Other suitable surfactants include, for example, dipalmitoyl phosphatidylethanolamine (DPPE), dipalmitoyl phosphatidylinositol (DPPI).

The force control agent may include or consist of one or more surface active materials, in particular materials that are surface active in the solid state, which may be water soluble or water dispersible, for example lecithin, in particular soya lecithin, or substantially water insoluble, for example solid state fatty acids such as oleic acid, lauric acid, palmitic acid, stearic acid, erucic acid, behenic acid, or derivatives (such as esters and salts) thereof such as glyceryl behenate. Specific examples of such materials are phosphatidylcholines, phosphatidylethanolamines, phosphatidylglycerols and other examples of natural and synthetic lung surfactants; lauric acid and its salts, for example, sodium lauryl sulphate, magnesium lauryl sulphate; triglycerides such as Dynsan 118 and Cutina HR; and sugar esters in general. Alternatively, the force control agent may be cholesterol.

Other possible force control agents include sodium benzoate, hydrogenated oils which are solid at room temperature, talc, titanium dioxide, aluminium dioxide, silicon dioxide and starch. Also useful as force control agents are film-forming agents, fatty acids and their derivatives, as well as lipids and lipid-like materials.

The inclusion of an additive material in the dry powder formulation may suitably confer one or more of the following benefits: enhancing the powder's dispersability; protecting the formulation from the ingress of moisture; enhancing the speed and reproducibility of the process.

In a preferred embodiment the pharmaceutical additive is suitably located on the surface of the particles comprising the compound according to formula 1.

In a preferred embodiment the pharmaceutical additive is magnesium stearate.

In a preferred embodiment the pharmaceutical additive is leucine.

Lactose fines also modify the interaction between the compound according to formula 1 and carrier particles affecting aerosol performance. In view of the additional protection now conferred by the polymer of the invention to the protein or peptide held by non-covalent interaction, in one embodiment the dry powder formulation may comprise fine lactose which is in an amount of preferably >3% (w/w), more preferably >5% (w/w), more preferably >8% (w/w) of the formulation residing in a blister or capsule or other suitable dispensing receptacle.

Pharmaceutical Excipients

In a yet further embodiment, pharmaceutical composition comprising the compound according to formula 1 comprises a pharmaceutical excipient. Dry powder formulations for inhalation in the treatment of respiratory diseases are generally formulated by mixing a micronised active pharmaceutical ingredient with coarse carrier particles to give an ordered mixture. The carrier particles make the micronised active pharmaceutical ingredient less cohesive and improve its flowability. This makes the powder easier to handle during the manufacturing process. The micronised active particles tend to adhere to the surface of the carrier particles when stored in a dry powder inhaler device but are dispersed from the surfaces of the carrier particles on inhalation into the respiratory tract to give a fine aerosol. The larger carrier particles impact on the throat due to their inertia and are mostly deposited in the oropharyngeal cavity.

One embodiment may include carrier particles which are mixed with the polymer-protein nanocomplexes in a ratio of from 2000:1 to 5:1 by mass, especially from 200:1 to 20:1 by mass. The carrier particles may be composed of any pharmacologically inert material or combination of materials which is acceptable for inhalation. They are suitably composed of one or more crystalline sugars including monosaccharides, disaccharides, polysaccharides and sugar alcohols such as arabinose, glucose, fructose, ribose, mannose, sucrose, trehalose, lactose, maltose, starches, dextran, mannitol or sorbitol. An especially preferred carrier is lactose, for example lactose monohydrate or alpha lactose monohydrate or anhydrous lactose.

Preferably substantially all (by weight or volume) of the carrier particles have a diameter of 20 to 1000 μm, more preferably 50 to 500 μm, but especially 20 to 250 μm. The diameter of substantially all (by weight) of the carrier particles is suitably less than 355 μm. This provides good flow and entrainment characteristics and improved release of the active particles in the airways to increase deposition of the active particles in the lower lung.

It will be understood that throughout this specification the diameter of the particles referred to is the diameter of the particles as suitably determined by a Malvern Mastersizer or similar laser diffraction equipment.

EXAMPLES

Selected embodiments of the present invention will now be explained with reference to the examples. It will be apparent to those skilled in the art from this disclosure that the following descriptions of the embodiments are for illustration only and not for the purpose of limiting the invention as defined by the appended claims and their equivalents.

Materials

L-Glutamic acid γ-benzyl ester (99.0%), allyl bromide (97%), cysteamine hydrochloride (98%), triethylamine (99.0%), acetonitrile (ACN, anhydrous, 99.8%), methoxy-polyethylene glycol amine 2,000, dichloromethane (DCM, anhydrous, 99.8%), N,N-Dimethylformamide (DMF, anhydrous, 99.8%), tetrahydrofuran (THF, anhydrous, 99.9%), deuterated chloroform (99.8 atom % D), deuterium oxide (99.9 atom % D), deuterated methanol (99.8 atom % D), sodium phosphate dibasic (99.9%), sodium phosphate monobasic dehydrate (99.0%), phosphoric acid, *Micrococcus lysodeikticus* lyophilised cells, trypsin from bovine pancreas, poly(allyl amine) solution (Mw: 17,000 g $mol^{-1}$), L-leucine and D-(+)-trehalose dihydrate were purchased from Sigma Aldrich. Lysozyme molecular biology grade and BCA protein assay kit were supplied by AppliChem and ThermoFisher Technologies, respectively. Methyl 3,4,5-trihydroxybenzoate (98.0%), potassium carbonate anhydrous (99.0%), sodium hydroxide (97.0%), oxalyl chloride (98.0%), 2,2-dimethoxy-2-phenylacetophenone (99.0%), hydrochloric acid, magnesium sulphate dried, toluene, methanol, diethyl ether anhydrous, propan-2-ol, petroleum ether and ethyl acetate were supplied by Fisher Scientific. Triphosgene 98.0% was supplied by Alfa Aesar. All the chemicals were used as received without further purification. Anhydrous solvents were used as received and stored under dry and inert atmosphere. Thin layer chromatography (TLC) was carried out on pre-coated TLC sheets ALUGRAM® SIL G/UV254 purchased from Macherey-Nagel. TLCs were visualized by exposure to UV light (254 nm) followed by staining with $KMnO_4$.

Example 1: Polymer Synthesis 3,4,5-tris(allylloxy)benzoic acid methyl ester (1) (see FIG. 9). Methyl 3,4,5-trihydroxybenzoate (4.5 g, 25 mmol, 1.0 equiv) and $K_2CO_3$ (16.4 g, 119 mmol, 4.8 equiv), were added to a round bottomed flask. Anhydrous acetonitrile (125 mL) and allyl bromide (21.0 g, 174 mmol, 7.0 equiv) were then added to the mixture under $N_2$ atmosphere via syringe. The mixture was then heated to reflux and stirred whilst protected from the light. After 3 hours H NMR showed completed conversion of the aromatic alcohol functionalities into their corresponding allyl ethers. Volatiles were then removed under reduce pressure. Toluene (200 mL) was added to the resulting residue, and the insoluble salts were filtered and washed with additional portions of toluene (3×100 mL). The toluene fractions were combined and the solvent removed under pressure to give the desired product (1) as an oil which was used for the next step without further purification. Yield 7.5 g, 100%. $^1H$ NMR (400 MHz, CDCl$_3$, δ, ppm): 7.28 (s, 2H, CH$_{aromatic}$), 6.14-6.01 (m, $^3$H$_{allyl}$), 5.47-5.16 (m, 6H$_{allyl}$), 4.65-4.59 (m, 6H, OCH$_2$), 3.88 (s, 3H, CH$_3$O). $^{13}$C NMR (101 MHz, CDCl$_3$, δ, ppm): 166.7, 152.4, 142.0, 134.3, 133.1, 125.1, 118.0, 117.8, 108.9, 74.2, 70.0, 52.3. ESI-TOF mass spectrometry: expected m/z [M-H$^+$] theor. 305.13, found 305.12. FT-IR: 1715 cm$^{-1}$ (σ$_{C=O}$).

3,4,5-tris(allyloxy)benzoic acid (Structure 2) (see FIG. 9). To a solution of ester (1) (see FIG. 9) (7.5 g, 25 mmol, 1 equiv) in a CH$_2$Cl$_2$/MeOH (9:1 v/v), 160 mL of a methanolic solution of NaOH 3.33 N was added into a round bottomed flask obtaining a final alkali concentration of 2.82 N. The mixture was stirred at room temperature. After 14 hours TLC (petroleum ether/ethyl acetate 6:4) revealed the absence of starting material (1) (see FIG. 9). The solvents were then removed under reduced pressure; the resulting residue was mixed with deionised water (200 mL) and extracted with diethyl ether (3×100 mL) in order to remove any traces of unreacted ester starting material (1) (see FIG. 9). The aqueous phase was then acidified with HCl 2M to pH 2 and extracted with dichloromethane (3×100 mL). The combined organic layers were dried over magnesium sulfate, filtered, and the solvent removed under reduced pressure to give (2) (see FIG. 9) as an oil (yield 6.0 g, 84%). H NMR (400 MHz, CDCl$_3$, δ, ppm): 7.35 (s, 2H, CH$_{aromatic}$), 6-14-6.03 (m, $^3$H$_{allyl}$), 5.47-5.16 (m, 6H$_{allyl}$), 4.66-4.62 (m, 6H, OCH$_2$) $^{13}$C NMR (101 MHz, CDCl$_3$, δ, ppm): 171.4, 152.4, 142.0, 134.3, 133.1, 123.9.1, 118.0, 117.8, 108.9, 74.2, 70.0. ESI-TOF mass spectrometry: expected m/z [M-H+] theor. 291.32, found 291.41. FT-IR: 1687 cm$^{-1}$ (Y$_{C=O}$).

3,4,5-tris(allyloxy)benzoyl chloride (3) (see FIG. 9). Compound (2) (see FIG. 9) (1.00 g, 3.4 mmol, 1.0 equiv) was dissolved in anhydrous dichloromethane (50 mL). Dry DMF catalyst (2 drops) and oxalyl chloride (0.66 g, 5.2 mmol, 1.5 equiv) were added to the solution under N$_2$ atmosphere via syringe. The mixture was stirred at room temperature for 1 h until evolution of gas could no longer be observed. Volatiles were then removed under reduced pressure. The residue was redissolved in dichloromethane and the solvent removed under reduce pressure. This procedure was repeated several times in order to remove all traces of residual oxalyl chloride and provide analytically pure (3) (see FIG. 9) as orange viscous oil which was used for next step without further purification. Yield: 1.0 g, 100%. H NMR (400 MHz, CDCl$_3$, δ, ppm): 7.35 (s, 2H, CH$_{aromatic}$), 6.08-5.97 (m, $^3$H$_{allyl}$), 5.44-5.15 (m, 6H$_{allyl}$), 4.66-4.58 (m, 6H, OCH$_2$). $^{13}$C NMR (101 MHz, CDCl$_3$, δ, ppm): 167.6, 152.4, 144.3, 133.9, 132.6, 127.7.1, 118.2, 118.2, 110.9, 74.3, 70.2. FT-IR: 1749 cm$^{-1}$ (υ$_{C=O}$).

mPEG$_{2k}$ triallyl ether (4) (see FIG. 9). Methoxypolyethylene glycol amine 2.0 kDa (1.5 g, 0.75 mmol) was dissolved in toluene (50 mL) and solvent was then removed under reduce pressure. This process was repeated five times in order to remove traces of water from the PEG starting material before starting the reaction. Compound (3) (see FIG. 9) (1.00 g, 3.20 mmol, 4.2 equiv), methoxypolyethylene glycol amine 2.0 kDa (1.50 g, 0.75 mmol, 1.0 equiv) and anhydrous triethylamine (0.70 g, 6.90 mmol, 9.2 equiv) were dissolved in anhydrous dichloromethane (50 mL) under inert atmosphere. The mixture was stirred at room temperature overnight, after which time 1H NMR analysis showed that the reaction was completed (aromatics signals shifted from 7.35 ppm to 7.04 ppm). The solvent was then removed under reduced pressure and the resulting residue suspended in 60 mL of water. Insoluble starting material (3) (see FIG. 9) was removed by filtration, and the aqueous solution was extracted with diethylether (3×100 mL) to remove triethylamine and other non-water soluble impurities, and finally with dichloromethane (3×100 mL). Removal of the solvent from the combined dichloromethane organic layers gave (4) (see FIG. 9) as a waxy solid (yield: 1.6 g, 92%). 1H NMR (400 MHz, CDCl$_3$, δ, ppm): 7.04 (s, 2H, CH$_{aromatic}$), 6.75 (bs, 1H, NHCO) 6.08-5.97 (m, $^3$H$_{allyl}$), 5.44-5.15 (m, 6H$_{allyl}$), 4.64-4.57 (m, 6H, OCH$_2$), 3.64-3.50 (s, 180H, OCH$_2$ of PEG), 3.37 (s, 3H, OCH$_3$ of PEG). FT-IR: 1793 cm$^{-1}$ and 1654 cm$^{-1}$ (υNCO).

TriaminoPEG (5). Compound (4) (see FIG. 9) (1.60 g, 0.69 mmol, 1.0 equiv), cysteamine hydrochloride (0.90 g, 12.00 mmol, 16.0 equiv) and 2,2-dimethoxy-2-phenylacetophenone (DPAP) (0.06 g, 0.23 mmol, 0.3 equiv) were dissolved in methanol (5 mL). The mixture was then irradiated using a 36 Watt UV Lamp equipped with 4×9 W Light bulbs at 365 nm for 3 hours, until allyl signals could no longer be detected by H NMR. Methanol was then evaporated under reduced pressure and the resulting residue was suspended in water. The mixture was extracted with ethyl acetate in order to remove traces of DPAP and corresponding decomposition products. The aqueous phase was extracted with isopropanol:dichloromethane 3:1 after addition of NaCl. Solvent removal under reduced pressure from the combined organic layers provided (5) (see FIG. 9) as solid (1.5 g, 76%). H NMR (400 MHz, CD$_3$OD, δ, ppm): 7.24 (s, 2H, CH$_{aromatic}$), 4.22 (t, J=6.0 Hz, 4H, OCH$_2$), 4.14 (t, J=5.8 Hz, 2H, OCH$_2$), 3.85-3.50 (s, 180H, OCH$_2$ of PEG), 3.35 (s, 3H, OCH$_3$ of methoxy PEG), 3.20 (t, J=6.7 Hz, 6H, CH$_2$N), 2.90-2.78 (m, 12H, CH$_2$S), 2.18 (m, 4H, OCH$_2$CH$_2$CH$_2$S), 1.97 (m, 2H, OCH$_2$CH$_2$CH$_2$S).

γ-Benzyl-L-glutamate N-carboxyanhydride (NCA). L-Glutamic acid γ-benzyl ester (13.7 g, 57.8 mmol) was added to a dry round bottomed flask. Anhydrous THF (200 mL) and triphosgene (6.8 g, 23.0 mmol) were then added under nitrogen atmosphere. The mixture heated at 50° C. under stirring. The reaction mixture turned clear in about 1 h. The solution was then cooled down to room temperature and flushed with nitrogen 2 h to remove traces of gaseous co-products in solution. The solution was then concentrated under reduced pressure to a final volume of approximately 10 mL and added to 100 mL of petroleum ether. The resulting solid was filtered, washed with petroleum ether and recrystallized from THF:petroleum ether 1:1 (v/v) three times at 0° C. to give the desired product as crystalline solid (5.2 g, 35%). H NMR (400 MHz, CDCl$_3$, δ, ppm): 7.40-7.31 (m, 5H, CH$_{aromatic}$), 6.59 (s, 1H, NH), 5.13 (s, 2H, CH$_2$O), 4.38 (ddd, J=6.5, 5.4, 0.8 Hz, 1H, OCCHNH), 2.59 (t, J=6.9 Hz, 2H, O(O)CCH$_2$), 2.31-2.06 (m, 2H, CH$_2$). $^{13}$C NMR (101 MHz, CDCl$_3$, δ, ppm): 172.5, 169.5, 151.9, 135.3, 128.8, 128.7, 128.5, 67.2, 57.0, 30.0, 27.0. FT-IR: 1651, 1737, 1790, 1856 and 1965 cm$^{-1}$.

mPEG$_{2k}$-p(glutamic acid) copolymers: typical polymerization conditions and hydrolysis of benzyl ester repeating units. Compound (5) (see FIG. 9) (50 mg, 0.019 mmol) or commercially available methoxypolyethylene glycol amine 2.0 kDa (50 mg, 0.025 mmol) were dissolved in dry THF (50 mL) in a round bottom flask and cooled to 0° C. γ-Benzyl-L-Glutamate NCA (628 mg, 2.39 mmol), (250 mg, 0.940 mmol), (250 mg, 0.940 mmol), or (83 mg, 0.32 mmol) to form mPEG$_{2k}$-mik-(GA$_{30}$)$_3$, mPEG$_{2k}$-mik-(GA$_{10}$)$_3$, mPEG$_{2k}$-lin-GA$_3$, and mPEG$_{2k}$-in-GA$_{10}$ copolymers, respectively, was dissolved in anhydrous THF (100 mL), cooled to 0° C. and added to the solution containing the amino-PEG initiator. The mixture was stirred at 0° C. under inert atmosphere. After 5 days at 0° C. the conversion was found to be 70% as judged by $^1$H NMR analysis. 6, 2.35, 2.35, or 0.79 mL of 1.0 M NaOH aqueous solution to hydrolyse benzyl ester repeating units in $mPEG_{2k}$-mik-$(GA_{30})_3$, $mPEG_{2k}$-mik-$(GA_{10})_3$, $mPEG_{2k}$-lin-$GA_3$, and $mPEG_{2k}$-lin-$GA_{10}$ copolymers respectively, (2.5 equiv. of NaOH per benzyl group) were then slowly added under vigorous stirring. The reaction was left to stir for 2 days at room temperature, then the solvents were removed under reduce pressure. The residue was dissolved in distilled water (50 mL) and the resulting solution was dialysed (MWCO 1 kDa for linear $mPEG_{2k}$-lin-$GA_{10}$ copolymers or 3 kDa for $mPEG_{2k}$-lin-$GA_{30}$, $mPEG_{2k}$-mik-$(GA_{10})_3$ and $mPEG_{2k}$-mik-$(GA_{30})_{30}$ polymers). The solution was then freeze-dried and analysed by $^1H$ NMR and SEC. $mPEG_{2k}$-mik-$(GA_{30})_3$ yield: 178 mg, 60%. $^1H$ NMR (400 MHz, $D_2O$, δ, ppm): 7.15 (s, 2H, $CH_{aromatic}$), 4.38-3.99 (m, 94H, HNCHCO and 6H, $CH_2NH$), 3.70-3.47 (s, 180H, $OCH_2$ of PEG), 3.3 (s, 3H, $OCH_3$ of PEG), 3.18-2.90 (m, 12H, $CH_2SCH_2$), 2.4-1.6 (m, 679H, $CH_2CH_2COOH$ and 6H, $CH_2$). Mn (GPC, Dulbecco's Phosphate-Buffered Saline (DPBS))=4.8, Đ=1.3. $mPEG_{2k}$-mik-$(GA_{10})_3$ yield: 120 mg, 90%. $^1H$ NMR (400 MHz, $D_2O$, δ, ppm): 7.15 (s, 2H, $CH_{aromatic}$), 4.38-3.99 (m, 31H, HNCHCO and 6H, $CH_2NH$), 3.70-3.47 (s, 180H, $OCH_2$ of PEG), 3.3 (s, 3H, $CH_3O$ of PEG), 3.18-2.90 (m, 12H, $CH_2SCH_2$), 2.4-1.6 (m, 126H, $CH_2CH_2COOH$ and 6H, $CH_2NH$). Mn (GPC, DPBS)=3.7 kDa, Đ=1.30. $mPEG_{2k}$-/in-$GA_{30}$ yield: 140 mg, 80%. $^1H$ NMR (400 MHz, $D_2O$, δ, ppm): 4.38-3.99 (m, 35H, HNCHCO), 3.70-3.47 (s, 180H, $OCH_2$ of PEG), 3.3 (s, 3H, $CH_3O$ of PEG), 2.4-1.6 (m, 260H, $CH_2CH_2COOH$). Mn (GPC, DPBS)=11.0 kDa, Đ=1.2. $mPEG_{2k}$-/in-$GA_{10}$ yield: 71 mg, 81%. 1H NMR (400 MHz, $D_2O$, δ, ppm): 4.38-3.99 (m, 9H, HNCHCO), 3.70-3.47 (s, 180H, $OCH_2$ of PEG), 3.3 (s, 3H, $CH_3O$ of PEG), 2.4-1.6 (m, 37H, $CH_2CH_2COOH$). Mn (GPC, DPBS)=5.9 kDa, Đ=1.40.

Preparation of Polymer-Protein Nanocomplexes

The copolymers disclosed possess linear n-R or miktoarm n-R structures where the length of the hydrophilic n block (mPEG) is kept constant and that of protein-binding $R^1$, $R^2$ and $R^3$ arms was systemically varied. The number of repeating units in $R^1$, $R^2$ and $R^3$ block arms varied from 10 to 30 units, to give a library of Linear n-R with 10 units (referred to as L10) and n-R with 30 units (L30); and Miktoarm n-$(R10)_3$ (referred to as M30) and n-$(R30)_3$ (M90) copolymers. The copolymers and the lysozyme model protein were mixed in phosphate buffer (PB) (10 mM, pH 7.4) at relative molar charge ratios of 2.5 (ratio between the number of charged "q" monomers residues present in the copolymer and the lysine and arginine residues of the protein).

Spray-Drying Conditions

A laboratory scale spray-drying apparatus was used to prepare particles comprising the polymer-protein nanocomplexes copolymers with lysozyme as a model protein using the following conditions: total solids content: 1% (w/v), atomization air flow rate: 15 L $min^{-1}$, atomization air pressure: 2.5 bar, air outlet temperature: 65° C., liquid feed flow rate: 2.5 mL/min, drying air flow rate 17 kg $h^{-1}$ and drying gas pressure: 2.0 bar.

In Vitro Pulmonary Deposition

Figure 1:
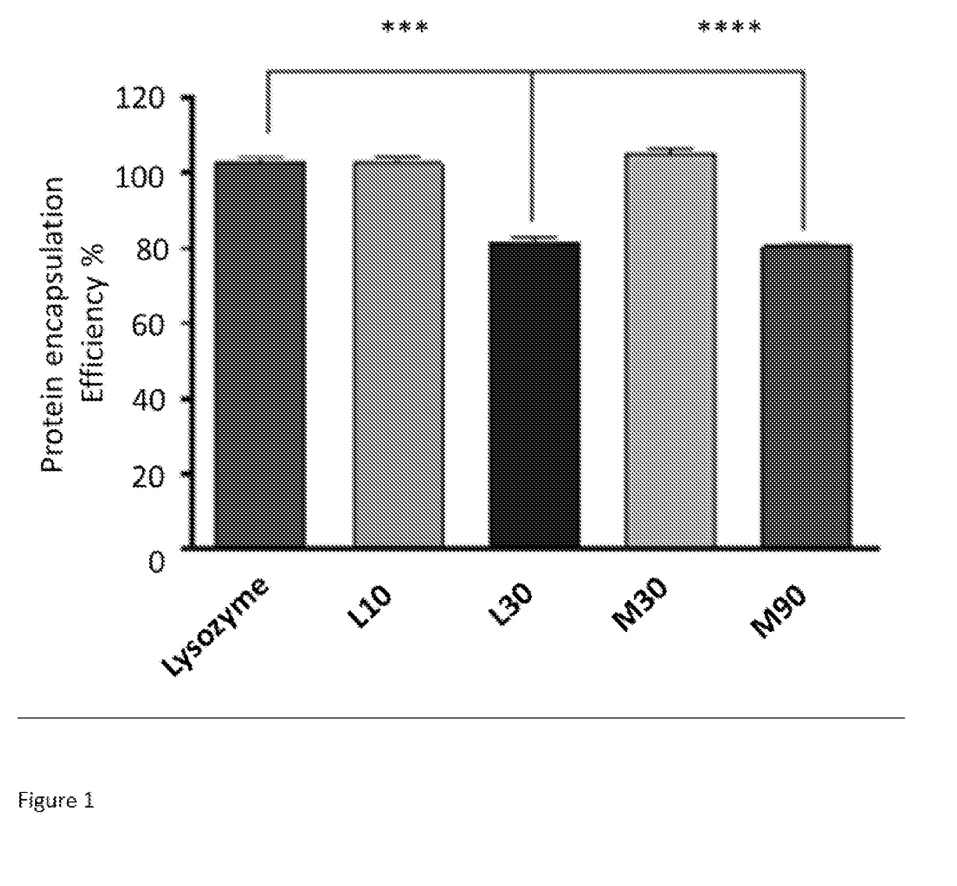
Figure 2:
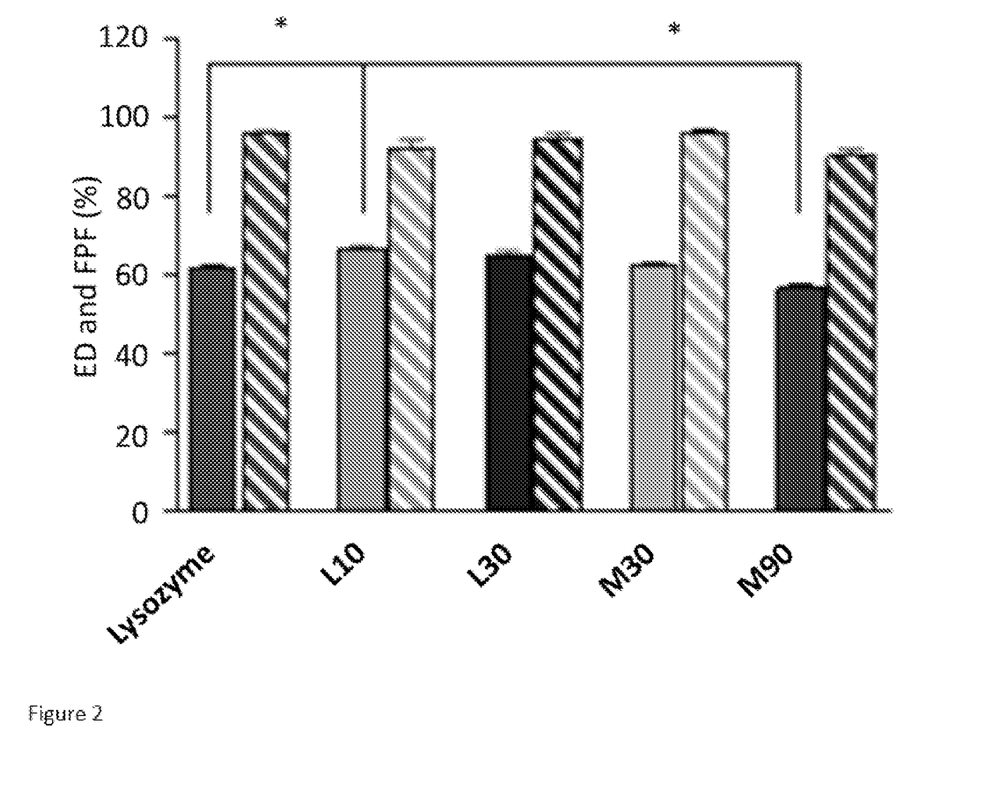

The aerodynamic properties of the particles comprising the copolymers were assessed using a fast screening impactor (FSI). A standard dispersion procedure was conducted for 4 s at an air flow rate of 60 L/min. The cut-off aerodynamic diameter was 5 μm. An amount of 12±1 mg of powder was loaded into blisters and aerosolised using a dry powder inhaler (DPI) device. Particles with an aerodynamic diameter lower than 5 μm deposited on a filter in the fine fraction collector. This filter was weighed before and after the air actuation, in order to determine the fine particle fraction (FPF), expressed as a percentage of the blister powder load. The emitted dose (ED) was calculated by accurately weighing the blister before and after aerosolisation. Each powder was tested in triplicate.

Protein Incorporation Efficiency

The amount of protein incorporated in the dry powders was evaluated by bicinchoninic acid assay (BCA) assay. Dry powders were first incubated in PB for 1 h under gentle stirring at room temperature—theoretical protein concentration 15-25 μg·$mL^{-1}$ (mass of protein assuming 100% protein incorporation). Then 150 μL of particle samples and 150 μL of BCA solution prepared as described by the manufacturer were mixed and heated at 56° C. for 60 min. Once cooled at 25° C., the absorbance was measured at λ=562 nm using a micro-plate reader SpectraMax M2. All the absorbance values were corrected by subtracting the values measured for relevant blank samples. Each measurement was performed in quadruplicate. The final protein incorporation efficiency (%) was calculated from the ratio between the amount of protein detected and that of protein utilised to prepare the liquid feed solution.

Recovery of Nanocomplexes from the Dry Powders in Aqueous Medium

To investigate whether the polymer-protein nanocomplexes could be recovered from the dry powders, the latter were incubated in PB (10 mM, pH 7.4) for 1 h under gentle stirring at room temperature at a protein concentration of 70 μg·$mL^{-1}$ (as quantified by BCA assay). The hydrodynamic diameter was measured by nanoparticle tracking analysis (NTA) using a Nanosight LM14. All measurements were performed at 25° C. The NTA 2.0 Build 127 software was used for data capturing and analysis. The samples were measured for 80 s.

Enzymatic Activity

In order to assess the enzymatic activity of the lysozyme model protein, a turbidimetric enzymatic assay was performed by measuring the decrease in optical density of a suspension of *Micrococcus lysodeikticus* lyophilized cells, a natural substrate for lysozyme, in PB. Nanocomplexes and also free lysozyme were extracted from the dry powders as previously described, at a protein concentration of 37 g·$mL^{-1}$ (as quantified by BCA assay). 10 mg of lyophilised cells were added to 20 mL of PB. 300 μL of this substrate suspension were added to 150 μL of particle solution and the decrease in optical density was measured at λ=460 nm as a function of time for 60 sec. The absorbance decay plots from 0 to 10 sec were fitted to a linear equation and the enzymatic activities were then determined from the slope of the fitted line. Not spray-dried free lysozyme was used in this work as reference (100% enzymatic activity).

Protein Protection Against Proteolytic Enzymes

Nanocomplexes were recovered from the dry powders as previously described, at a protein concentration of 37 μg $mL^{-1}$ (as quantified by BCA assay). 657 μg of trypsin (≥10,000 BAEE units/mg protein) were added to 4 mL of particle solution and the mixture was kept at room temperature for 3 h under gentle stirring. 480 g of poly(allyl amine) were then added to the solution, and the mixture was kept under gentle stirring for 1 h. Lysozyme activity was then quantified as previously described. All kinetic experiments were carried out in triplicate.

Results

Spray-dried powders were characterised by suitable $d_{50}$ diameter for inhalation (approximately 2.5 μm) and spherical morphology with smooth surface (see FIG. 8). Polymer-protein nanocomplexes were found to be efficiently loaded into the dry powders achieving up to 100% when the shorter polymers were used. However, under the conditions utilised in this example, spray-dried powders with the longer polymers decreased the protein loading content to around 80% (FIG. 1). In the powder dispersion experiment, the emitted dose (ED) and the fine particle fraction (FPF) were on average 95 and 65%, respectively which showed that around 65% of the dry powders were assumed to be fine particles optimal for inhalation (FIG. 2). Interestingly, linear L10 polymers showed a significant improvement of the aerodynamic properties reaching FPFs values up to 68%. Nevertheless, M90 copolymers decreased these values to 57%. The hydrodynamic diameter of the reconstituted polymer-protein nanocomplexes was not significantly different from that of nanocomplexes before spray-drying (FIGS. 3 and 4), indicating that the spray-drying process did not affect the stability of these nanoassemblies. Importantly, the polydispersity of these redispersed nanocomplexes decreased. All nanocomplexes recovered from the dry powders exhibited a decrease in protein activity as compared to lysozyme spray-dried with trehalose and leucine (FIG. 5). Following incubation of the particles in the presence of trypsin, lysozyme was recovered from the complexes by addition of poly(allyl amine), and its residual activity was assessed. In fact, poly(allyl amine) can ionically interact with A-B copolymers, inducing complex disassembly. All polymers, especially longer L30 and M90 copolymers, protected lysozyme against enzymatic degradation; whereas in the absence of polymer, lysozyme activity dropped to less than 40% of its initial value (FIG. 6).

Discussion

In this example, a series of spray-dried powders containing polymer-lysozyme nanocomplexes were created as formulations for pulmonary delivery of model protein therapeutic. Leucine was used as a force control agent which allowed the production of dry powders with FPFs as high as 68%.

Protein incorporation into the particles was found to be very efficient, with up to 100% of the protein added to the liquid feed solution being encapsulated. The presence of shorter polymers showed a significant improvement on protein incorporation efficiencies from 80 to 100% when compared to longer polymers. Importantly, high FPF was also retained, and in some cases slightly increased (from 62% to 68% with linear L10 copolymers) in trehalose-leucine-based dry powders.

Importantly, the size of the polymer-lysozyme nanocomplexes did not change significantly when compared to nanocomplexes before spray-drying and the polydispersity was found to be even smaller. These results were particularly impressive considering that very often the process of spray-drying can modify the size of nanoparticles once they are redispersed.

Lysozyme activity of polymer-protein nanocomplexes decreased when compared to that of the free protein, indicating that lysozyme was located in the “core” of these assemblies, where the enzyme was less accessible.

In this case, full activity of the lysozyme can be restored by treating the polymer-lysozyme nanocomplexes with poly (allyl amine) which, confirming that the low activity observed for the lysozyme-polymer nanocomplexes was due to reversible interactions of the protein with the copolymers, rather than to protein denaturation.

Finally, the ability of the polymer-lysozyme nanocomplexes to protect proteins from proteolytic enzymes was evaluated. Trypsin is an enzyme which cleaves proteins specifically at the carboxyl side of the aminoacids lysine and arginine. Lysozyme is particularly sensitive to trypsin due to its high content in those amino acids. An important decrease (>60%) in its enzymatic activity was observed when no polymer was added to the dry powder. In contrast, lysozyme was protected from trypsin digestion when polymers were present in the formulations. Surprisingly, when the longest L30 and M90 copolymers were used, close to full retention of the protein activity (up to 95-99%) was observed.

Example 2: Complement Activation Assay

Materials

Sheep erythrocytes and rabbit anti-sheep erythrocyte were purchased by Eurobio.

Methods

Polymer-lysozyme nanocomplexes or free lysozyme were kept in contact with normal human serum (NHS) and the residual haemolytic capacity was measured to study the complement activation. NHS was received from healthy volunteers, aliquoted and stored at −80° C. until use. Sheep erythrocytes were sensitised by rabbit anti-sheep erythrocyte antibodies at a final dilution of 1/800 v/v and these sensitised sheep erythrocytes were suspended at a final concentration of $1\times10^8$ cells $mL^{-1}$ in veronal-buffer saline (VBS2+, containing 0.5 mM Mg and 0.15 mM Ca2+). VBS2+ and NHS were mixed with polymer-lysozyme nanocomplexes or free lysozyme at final protein concentration of 1.116 mg $mL^{-1}$ so that the final dilution of NHS in the reaction mixture was 1/4 (v/v) in a final volume of 400 μl. The suspension was incubated at 37° C. for 60 min under gentle stirring. The mixture was then diluted 1/25 (v/v) in VBS2+ and different aliquots at different dilutions were added to a specific volume of sensitised sheep erythrocytes. The suspensions were incubated for 45 min at 37° C. under gentle stirring and the reaction was then stopped by adding ice-cold NaCl (0.15 M). The mixture was centrifuged at 2,000 rpm for 5 minutes to precipitate unlysed erythrocytes. The supernatant was collected and the optical density was measured at 415 nm with Dynex absorbance microplate reader (Dynex technologies, USA).

The presence of polymer-lysozyme nanocomplexes or free lysozyme without serum did not lead to hemolysis of the sensitized sheep erythrocytes at the protein concentrations investigated. Sample without serum was used here as positive control (100% complement activation, 0% sensitised sheep erythrocytes lysis) and employed to correct the absorbance values from the samples. Sample with serum and without particles was utilised as negative control (0% complement activation, 100% lysis). The data can be expressed in terms of CH50 units, defined as the serum dilution at which 50% haemolysis is observed. They can be calculated by a linear fit to a log-log version of the Von Krogh (equation 1). Particularly, in this study, the data was expressed as the percentage of complement activation relative to 100% complement activation observed with our positive control samples.

$$\text{Complement activation}(\%) = \frac{CH50_{sample} - CH50_{control}}{CH50_{control}} \qquad \text{Equation 1}$$

Where $CH50_{control}$ refers to CH50 of the positive controls (100% complement activation).

Results

Complement proteins present in the human serum are able to lyse sensitised sheep erythrocytes. However, when the presence of activating macromolecules such as proteins, less complement proteins are available in the medium to lyse the cells.

In this work, we observe that lysozyme, when incorporated into the core of polymer-protein nanocomplexes, had a lower interaction with complement proteins compared to the free lysozyme (FIG. 7). These results therefore suggest that these nanocomplexes can effectively decrease the immunogenicity of the entrapped proteins.

The invention claimed is:

1. A compound of the formula:

wherein n is an integer from 4 to 200 monomers, and wherein each of R1, R2 and R3 is independently a polymer chain comprising from about 4 to 200 monomers, wherein said monomers are selected from the group consisting of alanine, β-alanine, arginine, asparagine, aspartic acid, citrulline, cysteine, cysteine, cystathionine, glutamic acid, glutamine, glycine, histidine, homocysteine, hydroxyproline, hydroxylysine, isoleucine, leucine, lysine, methionine, ornithine, phenylalanine, phosphoserine, proline, pyrrolysine, serine, selenocysteine, threonine, tryptophan, tyrosine, valine, 4-aminobutyric acid and combinations thereof.

2. The compound of claim 1, wherein the polymer chains of R1, R2 and R3 each independently comprise substantially a monomer selected from alanine, β-alanine, arginine, asparagine, aspartic acid, citrulline, cysteine, cysteine, cystathionine, glutamic acid, glutamine, glycine, histidine, homocysteine, hydroxyproline, hydroxylysine, isoleucine, leucine, lysine, methionine, ornithine, phenylalanine, phosphoserine, proline, pyrrolysine, serine, selenocysteine, threonine, tryptophan, tyrosine, valine, and 4-aminobutyric acid.

3. The compound of claim 1, wherein the polymer chains of R1, R2 and R3 each independently comprise predominantly a monomer selected from alanine, β-alanine, arginine, asparagine, aspartic acid, citrulline, cysteine, cysteine, cystathionine, glutamic acid, glutamine, glycine, histidine, homocysteine, hydroxyproline, hydroxylysine, isoleucine, leucine, lysine, methionine, ornithine, phenylalanine, phosphoserine, proline, pyrrolysine, serine, selenocysteine, threonine, tryptophan, tyrosine, valine, and 4-aminobutyric acid.

4. The compound of claim 1, further comprising a physiologically active substance, wherein the compound forms an ester bond with the physiologically active substance.

5. The compound of claim 1, further comprising a physiologically active substance, wherein the compound forms a conjugate with the physiologically active substance.

6. The compound of claim 1, wherein each of R1, R2 and R3 is a linear polymer and does not comprise an aromatic hydrocarbon group or an aromatic heterocyclic group at an end of the polymer chain adjacent to the amine adjacent to each of R1, R2 and R3, respectively.

7. The compound of claim 1, wherein each of R1, R2 and R3 is a linear polymer and does not contain an aromatic hydrocarbon group or an aromatic heterocyclic group.

8. The compound of claim 1, wherein each of R1, R2 and R3 comprise a branching molecule.

9. The compound of claim 8, wherein the branching molecule comprises gallic acid.

10. The compound of claim 1, wherein the polymer chains of R1, R2 and R3 are each a branched polymer.

11. The compound of claim 10, wherein the branched polymer comprises gallic acid.

* * * * *